(12) United States Patent
Knutson et al.

(10) Patent No.: US 12,108,859 B2
(45) Date of Patent: Oct. 8, 2024

(54) METHOD AND DEVICE FOR LOW TEMPERATURE ERADICATION OR REMOVAL OF ECTOPARASITES

(71) Applicants: Rachel Knutson, Hopkins, MN (US); Lisa Rudquist, Hopkins, MN (US); James Parkhurst, Hopkins, MN (US)

(72) Inventors: Rachel Knutson, Hopkins, MN (US); Lisa Rudquist, Hopkins, MN (US); James Parkhurst, Hopkins, MN (US)

(*) Notice: Subject to any disclaimer, the term of this patent is extended or adjusted under 35 U.S.C. 154(b) by 0 days.

(21) Appl. No.: 18/108,750

(22) Filed: Feb. 13, 2023

(65) Prior Publication Data

US 2023/0329416 A1 Oct. 19, 2023

Related U.S. Application Data

(62) Division of application No. 16/994,319, filed on Aug. 14, 2020, now Pat. No. 11,576,476.

(60) Provisional application No. 62/976,776, filed on Feb. 14, 2020, provisional application No. 62/888,241, filed on Aug. 16, 2019.

(51) Int. Cl.
*A45D 24/22* (2006.01)
*A45D 24/00* (2006.01)
*A61B 17/50* (2006.01)
*A61F 7/00* (2006.01)

(52) U.S. Cl.
CPC ........ *A45D 24/22* (2013.01); *A45D 2024/002* (2013.01); *A45D 2200/155* (2013.01); *A61B 2017/505* (2013.01); *A61F 2007/0008* (2013.01); *A61F 2007/0052* (2013.01); *A61F 2007/006* (2013.01)

(58) Field of Classification Search
CPC ........ A45D 2024/002; A45D 2200/155; A45D 24/22; A61B 2017/505; A61F 2007/0008; A61F 2007/0052; A61F 2007/006; A61F 2007/0063; A61F 2007/0064; A61F 2007/0087; A61F 7/00
See application file for complete search history.

(56) References Cited

U.S. PATENT DOCUMENTS

2010/0071713 A1\* 3/2010 Simon .................... A45D 24/30
132/115
2013/0158546 A1\* 6/2013 Toomey ................. A61B 18/14
606/171

\* cited by examiner

*Primary Examiner* — Tigist S Demie
(74) *Attorney, Agent, or Firm* — R. John Bartz

(57) ABSTRACT

This disclosure relates generally to a system and method for the delivery of cooled air selectably using a device with removable component which directs cooled air to a desired area at or near the hair of a subject. The device may have one or more components which may be quickly and easily removed and replaced.

6 Claims, 2 Drawing Sheets

```
┌─────────────────────────────────────────────┐
│ CREATE A FLOW OF AIR OR REDUCE              │
│ TEMPERATURE OF A VOLUME OF AIR              │
└─────────────────────────────────────────────┘

┌─────────────────────────────────────────────┐
│ REMOVE HEAT FROM FLOW OF AIR                │
│ UNTIL BELOW AMBIENT AIR TEMPERATURE         │
└─────────────────────────────────────────────┘

┌─────────────────────────────────────────────┐
│ DEFINE A SECTION OF HAIR                    │
└─────────────────────────────────────────────┘

┌─────────────────────────────────────────────┐
│ INTRODUCE LUBRICATING LIQUID AT OR          │
│ NEAR BASE OF HAIR SECTION                   │
└─────────────────────────────────────────────┘

┌─────────────────────────────────────────────┐
│ DISPERSE LUBRICATING LIQUID                 │
│ THROUGHOUT BASE OF HAIR SECTION             │
└─────────────────────────────────────────────┘

┌─────────────────────────────────────────────┐
│ ORGANIZE HAIR SECTION                       │
└─────────────────────────────────────────────┘

┌─────────────────────────────────────────────┐
│ CREATE MOVEMENT OF THE VOLUME OF AIR        │
└─────────────────────────────────────────────┘

┌─────────────────────────────────────────────┐
│ DIRECT FLOW OF AIR AT HAIR SECTION          │
└─────────────────────────────────────────────┘

┌─────────────────────────────────────────────┐
│ MAINTAIN FLOW OF AIR AT HAIR SECTION        │
└─────────────────────────────────────────────┘

┌─────────────────────────────────────────────┐
│ MOVE FLOW OF AIR THROUGH HAIR SECTION       │
│ UNTIL TEMPERATURE OF LUBRICATING            │
│ LIQUID BELOW AMBIENT AIR TEMPERATURE        │
└─────────────────────────────────────────────┘

┌─────────────────────────────────────────────┐
│ INTODUCE ADDITIONAL LUBRICATING             │
│ LIQUID TO HAIR SECTION                      │
└─────────────────────────────────────────────┘

┌─────────────────────────────────────────────┐
│ MECHANICALLY REMOVE PARASITES AND           │
│ PARASITE EGGS FROM HAIR SECTION             │
└─────────────────────────────────────────────┘
```

FIG. 2

METHOD AND DEVICE FOR LOW TEMPERATURE ERADICATION OR REMOVAL OF ECTOPARASITES

RELATED APPLICATION

This application is a division of U.S. patent application Ser. No. 16/994,319 filed Aug. 14, 2020, now U.S. Pat. No. 11,576,476. U.S. patent application Ser. No. 16/994,319 claims the priority of U.S. Provisional Patent Application Ser. No. 62/888,241 filed Aug. 16, 2019 and U.S. Provisional Patent Application Ser. No. 62/976,776 filed Feb. 14, 2020.

FIELD OF THE INVENTION

This disclosure relates generally to a method for removing lice, lice eggs or other undesirable macroscopic parasites from skin or hair through the application of low temperature air or liquid and an air delivery device with a removable component which directs cool air to a desired area at or near the hair of a subject with one or more components which may be quickly and easily removed and replaced.

BACKGROUND OF THE INVENTION

Lice are scavengers. They feed on the dead skin and other debris found in hair, scalp and other parts of a body. They are usually only discovered once a colony has been established. An established colony will include both adult lice and eggs. Mature females lay between three to four eggs ("nits") per day. If the adults are removed but not the nits, those nits will hatch within eight days and reproduce. It is therefore necessary to kill or remove both the adults and the nits to prevent re-infestation. Lice procreate by attaching their eggs to human hair with saliva which makes the eggs difficult to remove. Lice may be removed using only a mechanical removal method by removing the adults and repeating the process after the nits have hatched. An example of a method using a comb in combination with a liquid to remove lice is disclosed in U.S. Pat. No. 6,006,758 issued to Thorne. Single session treatments are far more convenient and also reduce the risk of lice transfer.

Traditionally, removal of lice in a single session requires extremely high temperature air to kill both adults and nits. Heat is delivered to the lice via increasing the temperature of ambient air and delivering it directly to the lice using a device like a traditional hair dryer. Extremely high temperatures are uncomfortable and potentially damaging to both skin and hair. Various methods have been developed to avoid damage by applying heat only to hair, shielding more sensitive areas, or lowering the temperature. These methods of reducing discomfort also lower the effectiveness of the lice eradication. Air delivery devices such as hot air blowers and hair dryers are typically used for a variety of applications such as drying hair and cleaning or stripping surface layers. In addition, cold air blowers are sometimes used to style hair from a wet or dry condition. These traditional air delivery devices do not contemplate the application of cold air to an area to perform a non-cosmetic service.

In some prior methods, lice combs are used to mechanically remove both adult lice and nits, and can be used either alone or in combination with heat treatment. Usually, combinations including mechanical removal attempt to compensate for the ineffectiveness of the heat treatment. Lice removal combs, such as disclosed in U.S. Pat. No. 7,909,042 issued to Bachrach et al, utilize the width of the teeth of the comb to allow hair to pass tightly between the teeth in order to separate insects from the hair. As a slight variation, combing is used in combination with certain lubricating liquids in order to loosen the bonding agent adhering nits to hair. Combing methods can be generally effective without prior heat treatment. However, mere combing requires considerable time and effort to ensure that all lice are removed.

U.S. Pat. No. 5,261,427 issued to Dolev discloses a method of elimination of lice through the application of heated air to the hair of a person while directing the heated air away from the scalp in order to avoid discomfort. This method discloses the use of heated air with enough temperature to eradicate both adults and nits. This air delivery system is made less effective by the need to direct the air away from the scalp of the subject.

U.S. Pat. No. 6,685,969 issued to Van Scoik et al discloses a lice eradication treatment which applies a composition that releases, or absorbs, heat when brought in contact with water to the infested area. This change in temperature desiccates the nits in the case of a temperature increase, immobilizes the parasites, and increases the pH of the environment of the nit. Removal is then accomplished through combing or other mechanical removal. This method discloses temperature change through a chemical process and liquid transfer, not an air transfer.

U.S. Pat. Nos. 7,789,902 and 8,162,999 both issued to Clayton et al disclose methods of lice eradication that include heating a volume of air, and directing the air at the lice located in an area, while still eradicating a portion of the infestation. This method employs heated air at a temperature below the heat level in conventional treatments, but it encounters the same problems. In addition, the lower temperature is difficult to transfer uniformly through hair and is somewhat less effective.

Cold temperatures are also effective to immobilize or kill adult lice, and weaken the bond between nits and hair. Cold is advantageous because there is no need to reduce exposure to skin and hair. Below ambient air temperature treatments are used routinely in a clinical setting to reduce blood flow or nerve activity to a particular area reducing inflammation and swelling that causes pain around a joint or tendon. There is a substantial need for an effective, non-chemical, and potentially therapeutic system for delivering low temperatures to immobilize or kill lice which does not cause unnecessary discomfort. Cold temperatures directed to a scalp or head area effectively immobilize or kill adult lice and weaken the bond between nits and hair. An air delivery device that separates components contemplates the disposable nature of at least one of the components. Prior air delivery devices affix each piece in a way that requires removal of a fastener or some other more permanent fixture. The casing and interior components are not meant to be removable or replaceable. The removal of a component that comes into contact with the person is advantageous because the component can then be replaced for each use. The removed components can be sanitized or checked for dirt and debris in some fashion.

SUMMARY OF THE INVENTION

In a first preferred aspect, a volume of cooled air at a temperature lowered below ambient air is used to kill or immobilize ectoparasites. Humans and other mammals can tolerate, and in some instances benefit from, exposure to temperatures much lower than what is required to immobilize or kill ectoparasites such as lice. Where the cooled air immediately immobilizes ectoparasites, it renders them incapable of eluding mechanical removal. Immobilization may be required in the case of adult lice where said ectoparasite is able to move or adhere to hair in a manner sufficient to elude traditional methods of removal.

According to the preferred method of the present invention, head lice are removed along with nits after application of lowered temperatures to the hair. The hair may be arranged prior to, or simultaneously with, the application of liquid. An alternate variation of the preferred method includes application of a liquid to a certain portion and location on hair prior to an application of cooled air. The combination of liquid and lowered temperatures immobilizes the adult lice and affects the bond between the nits and the hair. The compromised lice and nits may then be mechanically removed. In the preferred embodiment, the mechanical removal is accomplished by a removable component with tines as described below.

In another aspect, the low temperature of the treatment reduces the efficacy of the bonding agent used by the lice to attach nits to the base of hair. The exact chemical makeup of the bonding agent has evolved to produce a strong bond under certain specific conditions, and is known in the art. Where the agent's conditions are modified, the strength of the bond is compromised.

In another aspect, the method may include the selective application of a liquid lubricating agent such as water to hair before introduction of low temperature air to adult lice and nits. The liquid conducts heat away from the parasites, and may act as a barrier against the introduction of ambient air to warm the parasites after the initial application of cooled air. In addition, the lubrication facilitates the mechanical removal of parasites.

In another preferred aspect, the removable component is easily separable from the other components required to accomplish the movement and reduction in temperature of a volume of air. The other components may be an engine for rotating a fan, and temperature reduction components. The other components may be housed separately from the other components of the air delivery device. The temperature reduction components may be air directing housing which directs moving air across a metal coil containing refrigerant or other heat absorbing chemicals. A directing housing sufficient to allow the passage of cooled air from the temperature reduction components to the removable portion may be used. In the preferred embodiment, flexible tubing directs the cooled air from the other components to the removable component.

In the preferred embodiment, two or more tines are disposed on the removable component, and may be used to accomplish the mechanical removal of head lice along with nits after an application of low temperatures to the hair. The tines may have a generally tapering rectangular shape to allow hair to pass between each tine.

Alternatively an application of a liquid to a certain portion and location on hair prior to application of cooled air may be used. The hair may be arranged prior to, or simultaneously with, the application of liquid using the comb. The combination of liquid and low temperatures immobilizes the adult lice and affects the bond between the nits and the hair. The compromised lice and nits may then be mechanically removed by passing hair between two or more tines.

DESCRIPTION OF THE DRAWINGS

The drawings, which are not necessarily drawn to scale, illustrate generally, by way of example, but not by way of limitation, various embodiments discussed in this application.

FIG. 2 is a graphical illustration depicting the steps required to complete a preferred embodiment of the method.

DESCRIPTION OF EMBODIMENTS OF THE INVENTION

Figure 1:
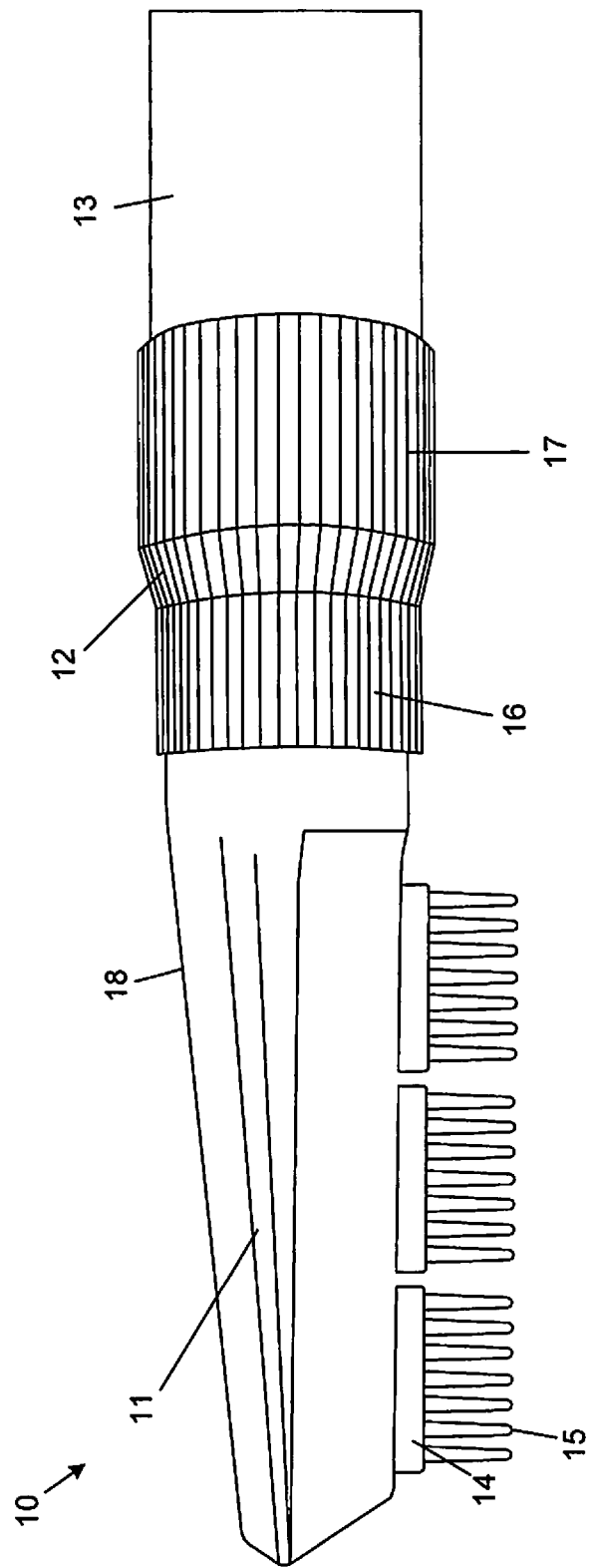
FIG. 1 is a planar side view of the air delivery device with removable component.

In the following detailed description, reference is made to the accompanying drawings, which form a part hereof, and in which is shown, by way of illustration, specific embodiments in which the inventive concepts may be practiced. These embodiments are described in sufficient detail to enable those skilled in the art to practice the invention, and it is to be understood that the embodiments may be combined or used separately, or that other embodiments may be utilized and that design, implementation, and procedural changes may be made without departing from the spirit and scope of the inventive concepts. The following detailed description provides examples, and the scope of the present invention is defined by the claims to be added and their equivalents.

The preferred embodiment of the air delivery device with removable component 10 is seen in FIG. 1. Hose 13 has a cavity and a generally cylindrical end piece which allows a volume of cooled air to pass through its interior. Hose 13 separates other components such as a motor and fan together with a cooling element from replaceable portion 11. In the preferred embodiment, ambient air is moved by a fan which is then directed across a coil containing a refrigerant to absorb heat. The cooled air is then directed through hose 13 to removable component 10. Sleeve 12 operates to releasably affix replaceable portion 11 relative to hose 13 such that replaceable portion 11 does not move relative to hose 13 during operation. Sleeve 12 has a lower portion 17 which accommodates a portion of hose 13 such that no air may escape as it passes between hose 13 and sleeve 12. In the preferred embodiment sleeve 12 holds hose 13 via a frictional engagement. Sleeve 12 may be of slightly smaller aperture than hose 13 and may deform to accommodate and firmly hold hose 13 in place. Sleeve 12 may be of some elastic material such that it may deform to hold hose 13 under slight pressure when hose 13 is inserted into lower portion 17 of sleeve 12. Sleeve 12 then tapers towards an upper portion 16 of sleeve 12.

Upper portion 16 of sleeve 12 accommodates a portion of replaceable portion 11 such that no air may escape as the air passes between sleeve 12 and replaceable portion 11. In the preferred embodiment sleeve 12 holds replaceable portion 11 via a frictional engagement. Sleeve 12 may be of slightly smaller aperture to firmly hold replaceable portion 11 in place. Sleeve 12 may be of some elastic material such that it may deform to hold replaceable portion 11 under slight pressure when replaceable portion 11 is inserted into upper portion 16 of sleeve 12.

Replaceable portion 11 has at least one rectangular shaped flange 14 surrounding an aperture open to the interior cavity of body 18. Flange 14 extends away from body 18 of replaceable portion 11 in a direction sufficient to direct air away from the hand of an operator such that the operator may control the direction of the flow of air while not being subjected or exposed to the air flow. Flange 14 may be of a size or shape sufficient to allow for the direction of the flow of air. In the preferred embodiment, flange 14 is directed at a right angle away from the direction of air flow in body 18 such that a user may hold body 18 comfortably. Additionally in the preferred embodiment, the aperture defined by flange 14 has a smaller width than the width of the interior cavity of body 18 to increase the pressure of air as the air flows from the interior of body 18 through the aperture.

Replaceable portion 11 has at least one tine 15 extending away from body 18 adjacent flange 14. In the preferred embodiment more than one tine 15 is disposed in a row along the bottom of body 18 such that the operator may arrange and direct the hair of a person through tines 15. In addition, tines 15 may be of a specific width to operate to remove any lice, nits or other parasites present on hair. In the preferred embodiment flange 14 directs air through the aperture in the same direction as tine 15 in order to allow the air flow to more easily reach the scalp beneath hair.

The preferred embodiment of the present method for the removal of an ectoparasite infestation is seen in FIG. 2. The preferred embodiment may first reduce the temperature of a volume of air to below ambient air temperature. Then, defining a section of hair having an infestation of undesirable adult lice, nits, or other ectoparasites. Third, introducing a volume of lubricating liquid at or near the base of the section of hair preferably contacting or nearly contacting any ectoparasites or their eggs in the section of hair. Fourth, disperse the lubricating liquid throughout the base of the section of hair such that the lubricating liquid is distributed evenly on the base of the section of hair. The dispersion of the lubricating liquid may be accomplished by any means of delivering a liquid to parted or organized hair. This organization of hair may be accomplished, for example, by hand or with two or more tines. It may also be accomplished simultaneously with the application of liquid or cooled air. Fifth, create movement of the volume of cooled air so that it may be directed in a specified general direction. The movement of the volume of cooled air may be accomplished by pressurizing a container of cooled air, through the use of a fan, or through the use of a blower. Sixth, direct the moving volume of cooled air at the section of hair. Direction of the moving volume of cooled air is accomplished in the preferred embodiment though the inclusion of a removable component as discussed below. Seventh, maintain the moving volume of cooled air at the section of hair for a predetermined period of time, until the lubricating liquid has reduced in temperature to a predetermined temperature, or until the lubricating liquid has at least partially solidified or frozen so as to kill or immobilize the ectoparasites and ectoparasite eggs. Eighth, direct the flow of cooled air through the section of hair until the temperature of the lubricating liquid is uniform. Ninth, optionally observe the ectoparasites in the section of hair to determine the effectiveness of the introduction of cold air. Tenth, introduce an additional second lubricating liquid to the section of hair. Eleventh, mechanically remove ectoparasites and their eggs from the section of hair. Mechanical removal may be preferably accomplished by passing through the section of hear with a comb that has tines that are close enough together to allow hair to pass through the tines while removing ectoparasites.

The examples and embodiments disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A device for removal of ectoparasites comprising:
   a removable component for receiving a volume of cooled air,
   the removable component having a sleeve and a replaceable portion,
   the sleeve having an upper portion and a lower portion,
   the replaceable portion having a body,
   the body having one or more flanges extending away from the body,
   the one or more flanges defining one or more apertures, and
   two or more tines extending away from the body,
   the sleeve holding a hose and the replaceable portion such that the hose and the replaceable portion do not move relative to each other during operation of the removable component,
   the sleeve being deformable to accommodate the hose and the replaceable portion,
   the removable component being removable from the hose after the operation,
   the body of the replaceable portion having a cavity open to the one or more apertures sufficient to accommodate the volume of cooled air whereby the volume of cooled air moves through the cavity and the one or more apertures,
   the one or more flanges having a sufficient size and orientation to direct the volume of cooled air from the cavity through the one or more apertures to hair,
   the two or more tines extending away from the body adjacent the one or more flanges such that the two or more tines direct or organize the hair in order to facilitate the application of the volume of cooled air to the hair.

2. The device for removal of ectoparasites according to claim 1 wherein:
   the body tapers away from the sleeve.

3. The device for removal of ectoparasites according to claim 1 wherein:
   the one or more apertures has a smaller width than the width of said cavity.

4. The device for removal of ectoparasites according to claim 1 wherein:
   the one or more flanges directs the volume of cooled air out of the one or more apertures in generally the same direction as the direction the two or more tines extend away from the body.

5. The device for removal of ectoparasites according to claim 1 wherein:
   the one or more flanges is directed at a right angle away from the direction of air flow in the body.

6. The device for removal of ectoparasites according to claim 1 wherein:
   the sleeve has a frictional engagement with the body and the hose.

* * * * *